US009816958B2

(12) United States Patent
Fujita et al.

(10) Patent No.: US 9,816,958 B2
(45) Date of Patent: Nov. 14, 2017

(54) GAS SENSOR, NOX SENSOR AND METHOD OF MANUFACTURING GAS SENSOR

(75) Inventors: Hiroki Fujita, Kasugai (JP); Hiroyuki Shindo, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 1418 days.

(21) Appl. No.: 12/407,931

(22) Filed: Mar. 20, 2009

(65) Prior Publication Data

US 2009/0242400 A1    Oct. 1, 2009

(30) Foreign Application Priority Data

Mar. 28, 2008 (JP) ................. 2008-086566

(51) Int. Cl.
*G01N 27/406* (2006.01)
*G01N 27/419* (2006.01)

(52) U.S. Cl.
CPC ....... *G01N 27/4067* (2013.01); *G01N 27/419* (2013.01)

(58) Field of Classification Search
CPC .. G01N 27/404–27/407; G01N 27/409; G01N 27/417; G01N 27/419; G01N 27/4067; G01N 27/4071; G01N 27/41
USPC ...... 204/421–429, 410, 411; 205/783.5–785; 73/23.31–23.32
See application file for complete search history.

(56) References Cited

U.S. PATENT DOCUMENTS

| 4,282,080 A | 8/1981 | Müller et al. |
| 4,798,693 A | 1/1989 | Mase et al. |
| 5,427,672 A | 6/1995 | Böcker et al. |
| 6,224,727 B1 | 5/2001 | Miyata et al. |
| 6,270,639 B1 * | 8/2001 | Lenfers et al. ............... 204/425 |
| 6,344,119 B2 | 2/2002 | Kato et al. |
| 6,579,436 B2 * | 6/2003 | Wang et al. .................. 204/425 |
| 2002/0139671 A1 * | 10/2002 | Kato .................. G01N 27/4067 204/431 |
| 2006/0220159 A1 | 10/2006 | Matsuo et al. |
| 2007/0017806 A1 * | 1/2007 | Furuta et al. ................. 204/424 |
| 2008/0105545 A1 * | 5/2008 | Nakagaki et al. ............ 204/424 |

FOREIGN PATENT DOCUMENTS

| EP | 0 678 740 A1 | 10/1995 |
| EP | 1 014 083 A2 | 6/2000 |
| JP | 60-228955 A1 | 11/1985 |
| JP | 2003-014690 A1 | 1/2003 |

(Continued)

*Primary Examiner* — Luan Van
*Assistant Examiner* — Maris R Kessel
(74) *Attorney, Agent, or Firm* — Burr & Brown, PLLC (57) ABSTRACT

It is an object of the present invention to provide a NOx sensor for accurately obtaining the resistance value of a heater. When a second layer is laminated immediately above a first layer on which the heater for electrically heating the proximity of an inner space of the NOx sensor and two heater leads having substantially same shape which are energizing paths to the heater are formed, the second layer on which at least one of leads is formed out of a first lead for electrically connecting a reference electrode to outside, a second lead for electrically connecting a measuring electrode to outside, and a third lead for electrically connecting a plurality of pump electrodes to outside, the lead formed on the second layer is arranged so as not to overlap any of two heater leads in a laminating direction of the first layer and the second layer.

6 Claims, 5 Drawing Sheets

(56) References Cited

FOREIGN PATENT DOCUMENTS

| | | |
|---|---|---|
| JP | 2006-284223 A1 | 10/2006 |
| JP | 2006-300923 A1 | 11/2006 |
| JP | 2009-052973 A1 | 3/2009 |
| WO | WO 2007015366 A1 * | 2/2007 |

* cited by examiner

| LEAD ARRANGEMENT | OVERLAPPING RATIO | $R_{L1}$ (Ω) | $R_{L2}$ (Ω) |
|---|---|---|---|
| SYMMETRICAL | D1/D2=0 | 2.236 | 2.233 |
| ASYMMETRICAL (WITHOUT OVERLAPPING) | D1/D2=0 | 2.232 | 2.231 |
| ASYMMETRICAL (PARTLY OVERLAPPING) | D1/D2=0.2 | 2.235 | 2.221 |
| ASYMMETRICAL (PARTLY OVERLAPPING) | D1/D2=0.5 | 2.241 | 2.197 |
| ASYMMETRICAL (PARTLY OVERLAPPING) | D1/D2=0.8 | 2.242 | 2.158 |
| ASYMMETRICAL (ENTIRELY OVERLAPPING) | D1/D2=1 | 2.240 | 2.141 |

GAS SENSOR, NOX SENSOR AND METHOD OF MANUFACTURING GAS SENSOR

BACKGROUND OF THE INVENTION

Field of the Invention

The present invention relates to a gas sensor composed with an oxygen ion conductive solid electrolyte, and particularly relates to a NOx sensor.

Description of the Background Art

Conventionally, various measuring devices have been used for determining a concentration of a desired gas component in a measurement gas. A known device of measuring a NOx concentration in a measurement gas such as a combustion gas, for example, employs a Nox sensor formed with an oxygen ion conductive solid electrolyte, such as zirconia ($ZrO_2$) (see Japanese Patent Application Laid-Open No. 8-271476, for example).

According to a Nox sensor disclosed in Japanese Patent Application Laid-Open No. 8-271476, $O_2$ in a measurement gas introduced from outside is previously removed by pumping in the first internal space so as to make the measurement gas to be in a state of low oxygen partial pressure (a state in which oxygen partial pressure is lowered to the extent that measurement of NOx is not affected by the presence of $O_2$ in the measurement gas), and then, the measurement gas is introduced into the second internal space. NOx is reduced at the measuring electrode by applying a constant voltage between the measuring electrode containing such as Pt and Rh provided in the second internal space and the reference electrode provided in the air. The NOx concentration is to be detected based on the current value of the current flowing at that time between the measuring electrode and the reference electrode, the current value being proportional to the NOx concentration.

The heater for electrically heating the NOx sensor is provided inside the NOx sensor. When detecting NOx in the aforementioned manner, heating is performed by the heater such that temperatures of the first and second internal spaces (and temperatures of electrodes provided for each internal space) satisfy the predetermined condition. In addition, the heating also helps to enhance oxygen ion conductivity of solid electrolyte composing the NOx sensor.

According to the Nox sensor disclosed in Japanese Patent Application Laid-Open No. 8-271476, the heating temperature of the heater is controlled on the basis of electric resistance value (resistance value) of the heater when applying current. Accordingly, it is necessary to accurately obtain the resistance value of the heater to control the heating temperature with precision.

The resistance value can be obtained by subtracting the resistance values of two leads (heater leads) connected to the both ends of the heater from the entire resistance value combining the heater and the two heater leads. According to the above, if two heater leads are provided in a manner that the resistance values are equal to each other, the resistance value of the heater can be obtained by subtracting the doubled value of the resistance value of one of the heater leads. In this case, it is necessary to ensure that the resistance values of the two heater leads are equal to each other in order to accurately obtain the accurate resistance value of the heater.

SUMMARY OF THE INVENTION

The present invention relates to a gas sensor composed with an oxygen ion conductive solid electrolyte, and more particularly to a heater part thereof.

According to the invention, a gas sensor is formed by laminating a plurality of solid electrolyte layers on each of which a predetermined circuit pattern is formed, and specifies concentration of a predetermined gas component in a measurement gas on the basis of current flowing within solid electrolyte by decomposing the predetermined gas component, the gas sensor comprising: an internal space to which the measurement gas is introduced; a reference gas space to which a reference gas is introduced; a plurality of pump electrodes provided to face each of the internal space and an external space; a measuring electrode provided to face the internal space; a reference electrode provided to face the reference gas space; an oxygen partial pressure controlling pump cell composed of the plurality of pump electrodes and solid electrolyte existing among the plurality of pump electrodes, for pumping in and out oxygen between the internal space and the external space; a measuring pump cell composed of the measuring electrode, the reference electrode and solid electrolyte existing therebetween, in which current flows in accordance with the amount of oxygen generated by decomposing the predetermined gas component within the internal space; a heater for electrically heating the proximity of the internal space, which is provided on a first layer of the plurality of solid electrolyte layers; two heater leads having substantially same shape which are energizing paths to the heater and provided on the first layer; a first lead for electrically connecting the reference electrode to outside; a second lead for electrically connecting the measuring electrode to outside; and a third lead for electrically connecting the plurality of pump electrodes to outside; wherein at least one of the first, second and third leads is formed on a second layer laminated immediately above the first layer, and arranged so as not to overlap any of the two heater leads in a laminating direction of the first layer and second layer.

As such, any of the two heater leads is not subjected to deformation by providing other leads on the layer above, allowing the gas sensor to obtain a heating temperature as well as a resistance value of the heater accurately on the basis of the entire resistance value and a resistance value of one heater lead.

It is therefore an object of the present invention to provide a gas sensor allowing to obtain a resistance value of a heater accurately.

These and other objects, features, aspects and advantages of the present invention will become more apparent from the following detailed description of the present invention when taken in conjunction with the accompanying drawings.

DETAILED DESCRIPTION OF THE INVENTION

<Gas Sensor>

Figure 1:
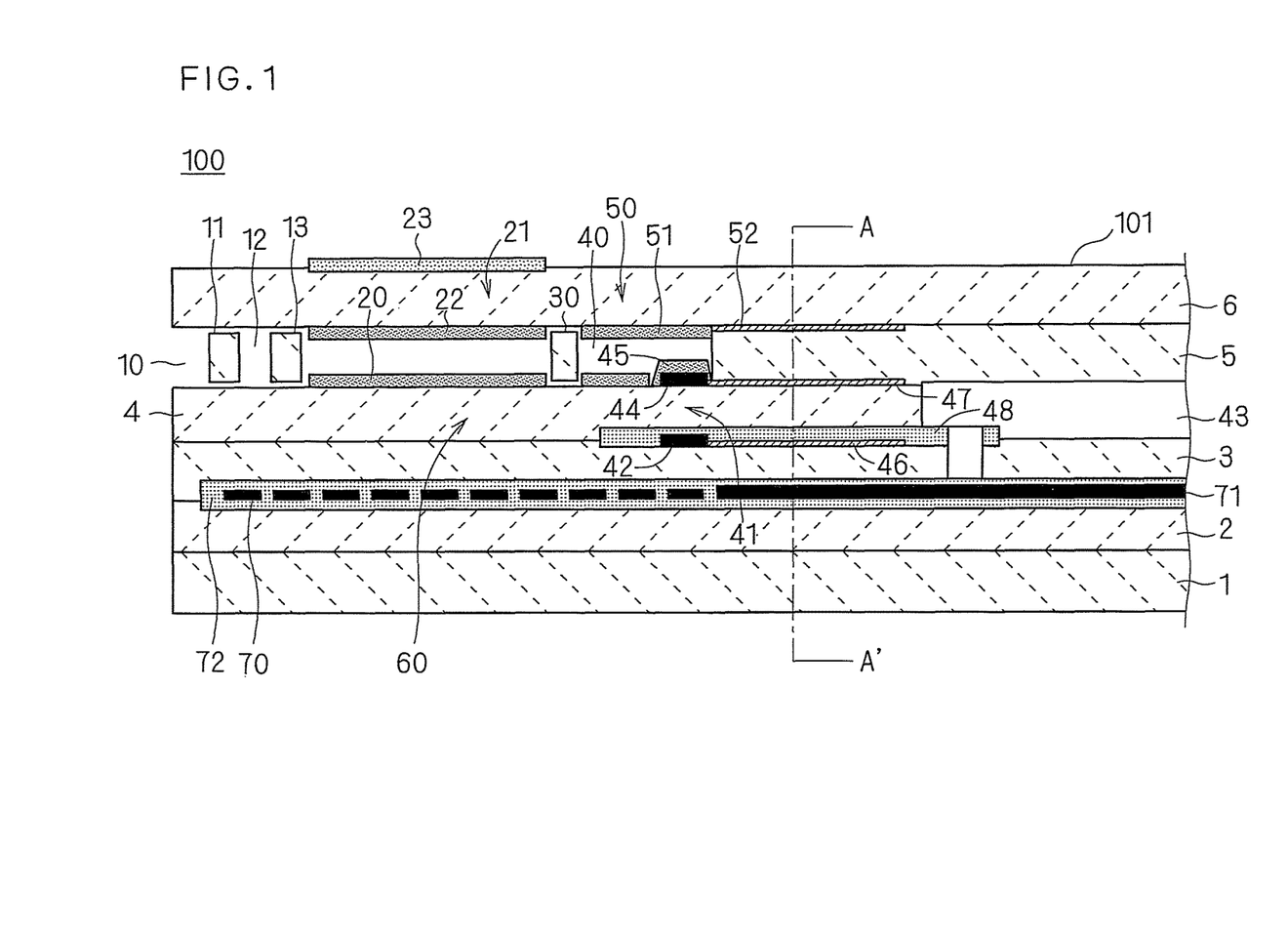
FIG. 1 is a cross sectional diagram schematically showing a configuration of the proximity of an end portion of a gas sensor 100 including a sensor element 101 according to a preferred embodiment.

FIG. 1 is a cross sectional diagram schematically showing a configuration of the proximity of an end portion of a gas sensor 100 including a sensor element 101 according to a preferred embodiment. The gas sensor 100 detects a predetermined gas component in a gas to be an object of measurement (measurement gas), and further measures its concentration. The present embodiment will be described taking an example where the gas sensor 100 is a NOx sensor for detecting nitrogen oxide (NOx) as an object component. The gas sensor 100 includes a sensor element 101 consisted of an oxygen ion conductive solid electrolyte such as zirconia ($ZrO_2$).

Specifically, the sensor element 101 includes a structure in which a first substrate layer 1, a second substrate layer 2, a third substrate layer 3, a first solid electrolyte layer 4, a spacer layer 5, and a second solid electrolyte layer 6 are laminated in this order from the bottom seen in Figure, each of the layers being consisted of an oxygen ion conductive solid electrolyte.

The sensor element 101 is manufactured by forming a laminated body consisted of green sheets including oxygen ion conductive solid electrolyte such as zirconia as a ceramics component, then cutting and burning the laminated body. Roughly mentioned, the laminated body is formed by the following steps of; forming a penetrating portion on a plurality of green sheets, each of which corresponds to each layer of the sensor element, by punching or the like to form an internal space, printing a predetermined circuit pattern with a predetermined paste in accordance with a laminating position, and sequentially laminating these green sheets after printing and applying a bonding paste on each green sheet as an adhesive. A publicly known screen printing process is available for printing a pattern and an adhesive. Also, a publicly known drying process is available for a drying process after printing. It is preferable to use a green sheet with thickness of several tens to several hundreds of µm (e.g., 150 µm) and to form a paste film to be a circuit pattern with thickness of some several µm.

A gas inlet 10, a first diffusion control part 11, a buffer space 12, a second diffusion control part 13, a first internal space 20, a third diffusion control part 30 and a second internal space 40 are adjacently formed in this order in communication with one another between a lower surface of the second solid electrolyte layer 6 and an upper surface of the first solid electrolyte layer 4 at the end portion of the sensor element 101. The gas inlet 10, the buffer space 12, the first internal space 20 and the second internal space 40 are provided by hollowing out the spacer layer 5, which is an internal space with an upper portion sectioned by the lower surface of the second solid electrolyte layer 6, an lower portion sectioned by the upper surface of the first solid electrolyte layer 4, and a side portion sectioned by a side surface of the spacer layer 5. Each of the first diffusion control part 11, the second diffusion control part 13 and the third diffusion control part 30 is provided as two horizontally long slits (with an opening having a longitudinal direction in a direction perpendicular to Figure). A part from the gas inlet 10 to the second internal space 40 is also referred to as a gas distribution part.

A reference gas inlet space 43 is provided between an upper surface of the third substrate layer 3 and a lower surface of the spacer layer 5 at a position which is far from the end portion than the gas distribution part is. The reference gas inlet space 43 is an internal space with an upper portion sectioned by the lower surface of the spacer layer 5, a lower portion sectioned by the upper surface of the third substrate layer 3, and a side portion sectioned by a side surface of the first solid electrolyte layer 4. For example, air is introduced to the reference gas inlet space 43 as a reference gas.

The gas inlet 10 is a part which is open to an external space, and a measurement gas is brought into the sensor element 101 from the external space through the gas inlet 10.

The first diffusion control part 11 provides a predetermined diffusion resistance to the measurement gas brought into from the gas inlet 10.

The buffer space 12 is provided in order to counteract concentration fluctuation of the measurement gas caused by pressure fluctuation (pulsation of exhaust pressure if a measurement gas is an emission gas of automobiles) of the measurement gas in the outside.

The second diffusion control part 13 provides a predetermined diffusion resistance to the measurement gas brought into the second diffusion control part 13 from the buffer space 12.

The first internal space 20 is provided as a space for controlling oxygen partial pressure in the measurement gas introduced through the second diffusion control part 13. The oxygen partial pressure is controlled by operating a main pump cell 21.

The main pump cell 21 is an electrochemical pump cell composed of an inside pump electrode 22 provided on an almost whole surface in a part of the lower surface of the second solid electrolyte layer 6 facing the first internal space 20, an outside pump electrode 23 provided in a region corresponding to the inside pump electrode 22 on an upper surface of the second solid electrolyte layer 6 to be exposed to the external space, and a part of the second solid electrolyte layer 6 interposed between those electrodes. The inside pump electrode 22 and the outside pump electrode 23 are formed as porous cermet electrodes (e.g. cermet electrodes of Pt and $ZrO_2$ including Au by 1%) which are oblong in a plane view. Further, the inside pump electrode 22 is formed using material in which reduction ability to an NO component in the measurement gas is weakened, or material without reduction ability.

The main pump cell 21 is provided with a variable power source not shown (first power source) outside the sensor element 101. The variable power source applies a desired pump voltage (first pump voltage) between the inside pump electrode 22 and the outside pump electrode 23 to flow pump current (first pump current) in a positive direction or a negative direction between the outside pump electrode 23 and the inside pump electrode 22, allowing to pump out oxygen in the first internal space 20 to the external space or to pump in oxygen in the external space into the first internal space 20.

The third diffusion control part 30 provides a predetermined diffusion resistance to the measurement gas brought into the second internal space 40 from the first internal space 20.

The second internal space 40 is provided as a space for performing a process to measure concentration of nitrogen oxide (NOx) in the measurement gas introduced through the third diffusion control part 30.

A NOx concentration can be measured by operating a measuring pump cell 41. The measuring pump cell 41 is an electrochemical pump cell composed of a reference electrode 42 between the upper surface of the third substrate layer 3 and the first solid electrolyte layer 4, a measuring electrode 44 provided on the upper surface of the first solid electrolyte layer 4 facing the second internal space 40, spaced apart from the third diffusion control part 30, and the first solid electrolyte layer 4. Each of the reference electrode 42 and the measuring electrode 44 is a porous cermet electrode which is substantially oblong in a plane view. The measuring electrode 44 is composed of metal resolving NOx which is a measurement gas component, and of porous cermet consisted of zirconia. Therefore, the measuring electrode 44 serves as a NOx reduction catalyst for resolving NOx existing in the atmosphere of the second internal space 40.

The reference electrode 42 and the measuring electrode 44 are connected to a reference electrode lead 46 and a measuring electrode lead 47 which are electronic connecting wires between the sensor element 101 and outside, respectively. Each of the reference electrode lead 46 and the measuring electrode lead 47 are provided such that its end portion can be connected to an external terminal. The reference electrode 42 and the reference electrode lead 46 are surrounded by an air induction layer 48 consisted of porous alumina and leading to a reference gas introduction space.

Moreover, the measuring electrode 44 is covered with a fourth diffusion control part 45. The fourth diffusion control part 45 is a film consisted of alumina, and functions to limit the amount of NOx flowing into the measuring electrode 44.

The measuring pump cell 41 is provided with a DC power source not shown (second power source) for applying a pump voltage (second pump voltage), which is fixed value voltage, between the measuring electrode 44 and the reference electrode 42 to resolve NOx. As a result, oxygen generated in the atmosphere inside the second internal space 40 is pumped out to the reference gas inlet space 43. A pump current (second pump current) allowed to flow by the operation of the measuring pump cell 41 is detected by an ammeter not shown.

Also, with respect to the measurement gas introduced through the third diffusion control part 30, oxygen partial pressure is previously controlled in the first internal space 20, and thereafter, oxygen partial pressure is further controlled in the second internal space 40 by an auxiliary pump cell 50. Accordingly, the gas sensor 100 can perform the measurement of a NOx concentration with high precision.

The auxiliary pump cell 50 is an auxiliary electrochemical pump cell composed of an auxiliary pump electrode 51 provided on substantially whole surface in a part of the lower surface of the second solid electrolyte 6 facing the second internal space 40, the second solid electrolyte 6, the spacer layer 5, the first solid electrolyte 4 and the reference electrode 42.

Similarly to the inside pump electrode 22, the auxiliary pump electrode 51 is formed using material in which reduction ability to an NO component in the measurement gas is weakened, or material without reduction ability. Further, the auxiliary pump electrode 51 is connected to a pump electrode lead 52 which is an electronic connecting wire to outside the sensor element 101. Also, the aforementioned inside pump electrode 22 and the outside pump electrode 23 are connected to electrode leads not shown in FIG. 1, respectively, which are electronic connecting wires to outside the sensor element 101. These electrode leads are also provided such that their end portions can be connected to the external terminal.

The auxiliary pump cell 50 is provided with a DC power source not shown (third power source) outside the sensor element 101. The DC power source (third power source) applies a fixed voltage between the auxiliary pump electrode 51 and the reference electrode 42 to pump out oxygen in the atmosphere inside the second internal space 40 into the reference gas inlet space 43.

Moreover, the sensor element 101 includes an oxygen partial pressure detecting sensor cell 60 which is an electrochemical pump cell composed of the inside pump electrode 22, the reference electrode 42, the second solid electrolyte layer 6, the spacer layer 5 and the first solid electrolyte layer 4.

The oxygen partial pressure detecting sensor cell 60 detects oxygen partial pressure in the atmosphere of the first internal space 20 on the basis of an electromotive force generated between the inside pump electrode 22 and the reference electrode 42 which is caused by the difference of oxygen concentration between the atmosphere inside the first internal space 20 and a reference gas (air) of the reference gas inlet space 43. The detected oxygen partial pressure is used for feedback controlling the first power source. Specifically, a pump voltage applied to the main pump cell 21 is controlled so as to set oxygen partial pressure in the atmosphere of the first internal space 20 at a predetermined value which is lower enough to control oxygen partial pressure in the second internal space 40.

The sensor element 101 includes a heater 70 and heater leads 71 connected to both ends of the heater 70, which are formed to be interposed between the second substrate layer 2 and the third substrate layer 3 from above and below. The heater 70 is a resistance heating element for generating heat by power feeding through the heater leads 71 which are energizing paths from outside the sensor element 101. The heater 70 itself can be formed of platinum, for example. The heater 70 is buried over the whole area from the first internal space 20 to the second internal space 40. A heater insulating layer 72 consisted of alumina or the like is formed on an upper surface and a lower surface of the heater 70 and the heater leads 71 in order to obtain electronic insulation between the second substrate layer 2 and the third substrate layer 3.

The first internal space 20 and the second internal space 40 (and the electrodes provided for each) of the sensor element 101 can be heated and kept the heat at a predetermined temperature by heating by the heater 70. Heat generation by the heater 70 allows to enhance oxygen ion conductivity of solid electrolyte composing the sensor element 101.

In the gas sensor 100 having the aforementioned configuration, the measurement gas is provided with the measuring pump cell 41, the measurement with oxygen partial pressure constantly maintained at a fixed low value (value substantially not affecting the measurement of NOx) by operating the main pump cell 21 and the auxiliary pump cell 50. Accordingly, the second pump current is substantially proportional to the reduced NOx concentration, the second pump current flowing in the measuring pump cell 41 by pumping out oxygen generated by a reduction of NOx, thereby allowing to find out NOx concentration in the measurement gas.

<Relation Between Lead Arrangement and Calculation of Resistance Value>

Figure 2:
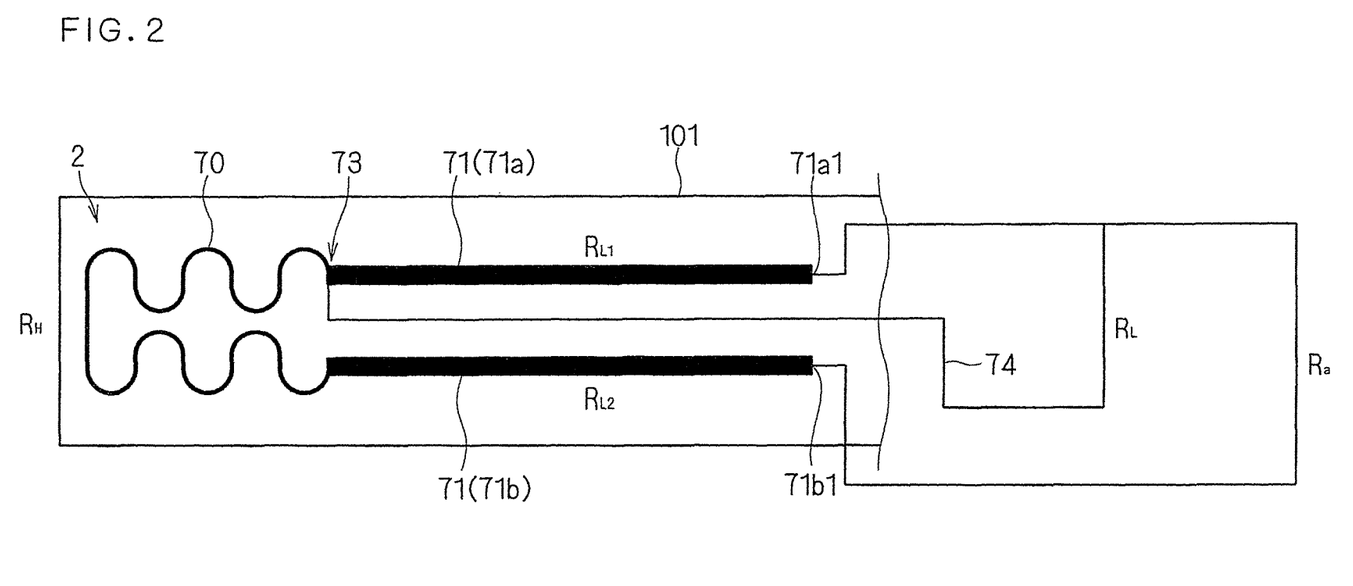
FIG. 2 is a diagram showing a planar structure of a heater 70.
Figure 3:
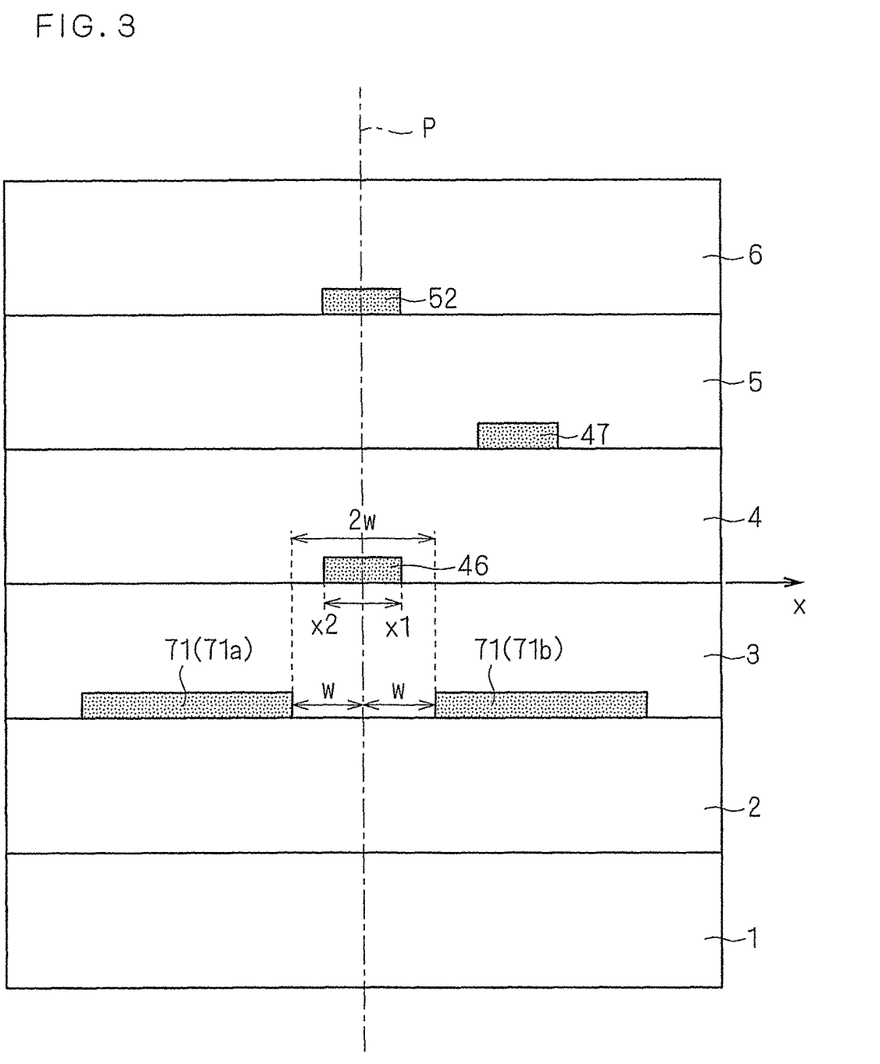
FIG. 3 is a view showing a lead arrangement of the sensor element 101 when a cross section A-A' of FIG. 1 is seen from the end of the element sensor 101.

FIG. 2 is a diagram showing a planar structure of a heater 70. FIG. 3 is a view showing a lead arrangement of the sensor element 101 when a cross section A-A' of FIG. 1 is seen from the end of the element sensor 101 (from the left side of FIG. 1).

As shown in FIG. 2, the heater 70 is provided on an upper surface of the second substrate layer 2 (between the second substrate layer 2 and the third substrate layer 3) at the end portion of the sensor element 101 so as to form a meandering shape in a plane view and to be axisymmetric to the center line of the longitudinal direction of the upper surface of the second substrate layer 2.

As described above, two heater leads 71 (71a, 71b) are provided on the upper surface of the second substrate layer 2 in a manner to be connected to the both ends of the heater 70. The heater leads 71a and 71b are provided so as to have substantially same shape and to be axisymmetric with each other to the center line of the longitudinal direction of the upper surface of the second substrate layer 2 (or to the perpendicular bisector P on a cross section of the sensor element 101 shown in FIG. 3). As shown in FIG. 3, letting the distance from each end portion of the heater leads 71a and 71b to the perpendicular bisector P be w, the heater leads 71a and 71b are to be provided at the distance of 2w. A resistance detecting lead 74 is provided on the upper surface of the second substrate layer 2 in a manner to be extracted from a connection part 73 of the heater 70 and the heater lead 71a. The resistance value of the resistance detecting lead 74 can be ignored.

Letting the resistance value of the heater 70 be $R_H$, the resistance value of the heater lead 71a be $R_{L1}$, and the resistance value of the heater lead 71b be $R_{L2}$, and further letting the resistance value between an edge portion 71a1 of the heater lead 71a and an end portion 71b1 of the heater lead 71b be $R_a$, and the resistance value between both ends of the heater lead (between the edge portion 71a1 and the connection part 73) be $R_L$, the resistance value $R_H$ of the heater can be obtained by the following equation:

$$R_H = R_a - (R_{L1} + R_{L2}) \quad (1)$$

As the resistance value of the resistance detecting lead 74 can be ignored, if it is possible to assume that the resistance values of two heater leads 71a and 71b are same, the equation (1) is to be as follows:

$$R_H = R_a - 2R_L \quad (2)$$

That is, the resistance value $R_H$ of the heater 70 can be obtained by measuring $R_a$ and $R_L$.

Consequently, in order to establish the equation (2), relating components are arranged to produce a state in which the resistance values of two heater leads 71a and 71b are same in the sensor element 101 according to the present embodiment.

Practically, the equation (2) can be accomplished by preferably defining the arrangement relation of the heater leads 71 and the reference electrode lead 46. More specifically, the reference electrode lead 46 is provided on the third substrate layer 3 (between the third substrate layer 3 and the first solid electrolyte layer 4) as described above, and at the same time, as shown in FIG. 3, the arrangement relation of the heater leads 71 and the reference electrode lead 46 is defined so as not to overlap with each other in a laminating direction (vertical direction seen in FIG. 3) in the cross-section perpendicular to the longitudinal direction of the sensor element 101.

FIGS. 4A to 4D and FIG. 5 are views for showing the arrangement relation described above. FIGS. 4A to 4D are diagrams showing all the cases of the arrangement relation between the heater leads 71 and a reference electrode lead 46. In FIGS. 4A to 4D, all the other layers except the second substrate layer 2 and the third substrate layer 3 are not shown for simplifying Figures.

Figure 4A:
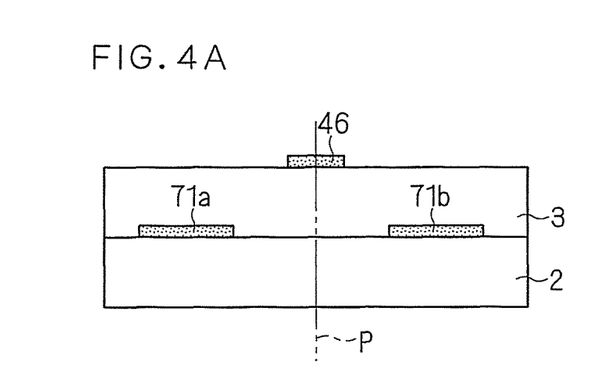
FIGS. 4A, 4B, 4C and 4D are diagrams showing all the cases of arrangement relation of heater leads 71 and a reference electrode lead 46.
Figure 4B:
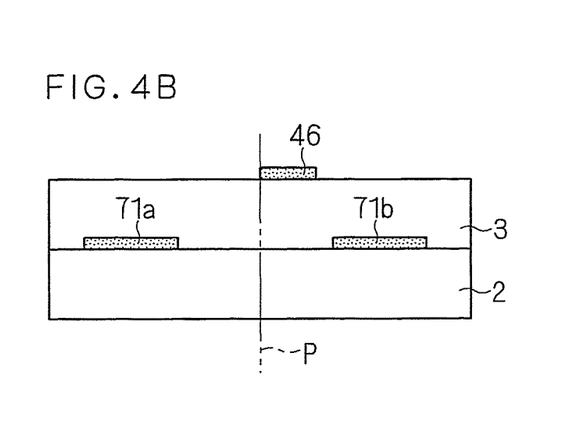
Figure 4C:
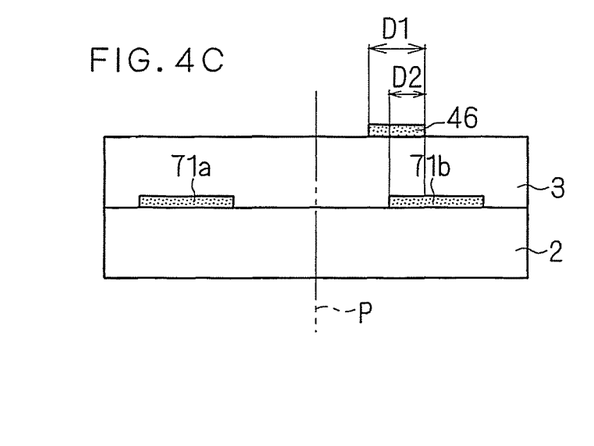
Figure 4D:
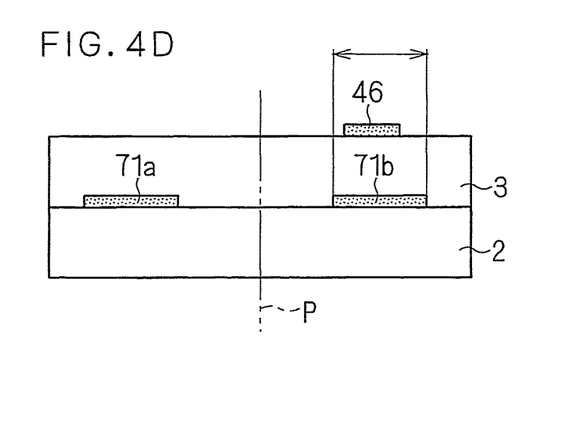

FIG. 4A shows the case where the reference electrode lead 46 does not overlap any of the heater leads 71 in the laminating direction, and is arranged to be symmetrical to the perpendicular bisector P. FIG. 4B shows the case where the reference electrode lead 46 does not overlap any of the heater leads 71 in the laminating direction, and is arranged to be asymmetrical to the perpendicular bisector P (the case where the reference electrode lead 46 is arranged to be situated nearer the heater lead 71b). FIG. 4C shows the case where the reference electrode lead 46 is arranged to partly overlap one of the heater leads 71. FIG. 4D shows the case where the entire reference electrode lead 46 overlaps one of the heater leads 71 in the laminating direction.

As shown in FIG. 4C, letting the width of the reference electrode lead 46 be D1, and the overlapping width of the reference electrode lead 46 and each of the heater leads 71 be D2, the ratio of D1 to D2 is referred to as the "overlapping ratio". In the case of FIGS. 4A and 4B, D1/D2=0, in the case of FIG. 4C, 0<D1/D2<1, and in the case of FIG. 4D, D1/D2=1.

Figure 5:
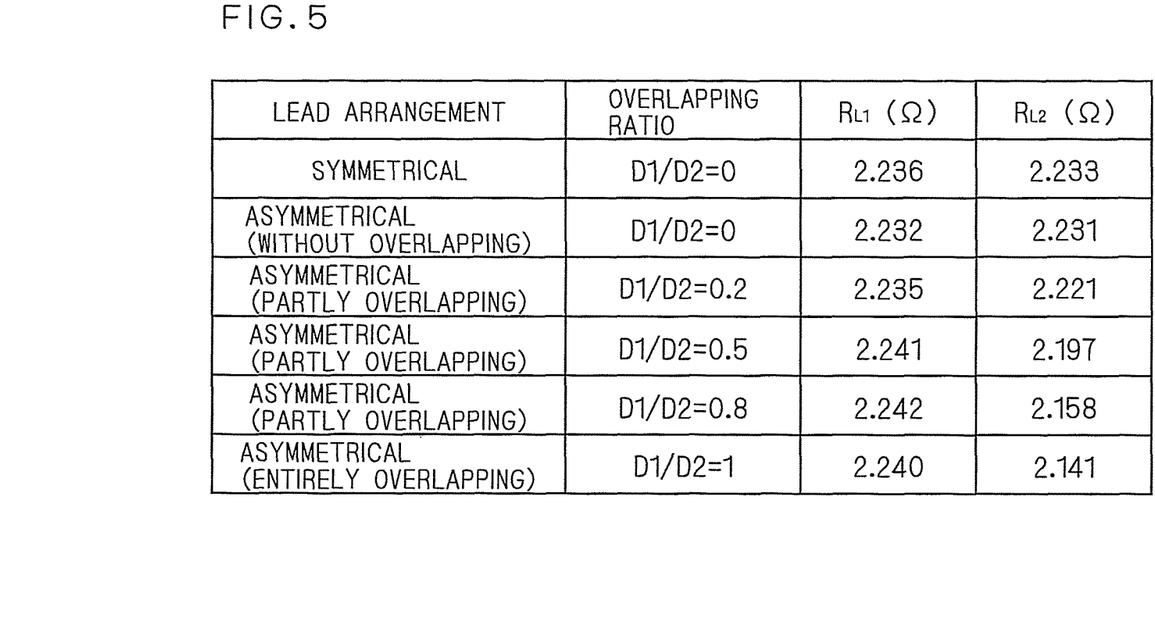
FIG. 5 is a view of listing the overlapping ratio in various arrangement relations shown in FIGS. 4A, 4B, 4C and 4D and the resistance values of two heater leads at that time.

FIG. 5 is a view of listing the overlapping ratio in various arrangement relations shown in FIGS. 4A, 4B, 4C and 4D and the resistance values of two heater leads 71 at that time. FIG. 5 shows the result in the case where the designed value of the resistance value of each of the heater leads 71 is 2.23Ω. In this case, the measuring electrode lead 47 and the pump electrode lead 52 are arranged as shown in FIG. 3.

As can be seen from the result shown in FIG. 5, while the resistance value of each of two heater leads 71 is almost same when the overlapping ratio is 0, the resistance value $R_{L2}$ of the heater lead 71b having an overlapping part is smaller than the resistance value $R_{L1}$ of the heater lead 71a not having an overlapping part when the overlapping ratio is larger than 0. That is, if only the reference electrode lead 46 is arranged so as not to overlap any of the heater leads 71 in the laminating direction, the resistance value of the heater 70 can be accurately calculated by the equation (2).

To describe more in detail, as shown in FIG. 3, when taking an X-axis with the perpendicular bisector P as an origin in a direction perpendicular to the perpendicular bisector P (horizontal direction seen in FIG. 3), and making the coordinates at positions of both ends of the reference electrode lead 46 as x1 and x2 (x1>x2), respectively, it is only necessary to arrange the reference electrode lead 46 to satisfy |x1|<w and |x2|<w.

The resistance of the heater lead 71 having the overlapping part gets smaller because printing films to become the heater leads 71 in the manufacturing process of the sensor element 101 are subjected to deformation. More specifically, in the case where a green sheet to be the third substrate layer 3 is laminated on a green sheet to be the second substrate layer 2 on which the printing films to become the heater leads 71 are applied, if the printing patterns of the reference electrode lead 46 and the heater leads 71 are formed to overlap with each other, the printing films to become the heater leads 71 are to be subjected to the deformation (unsymmetric pressure) induced to the presence of the printing film to become the reference electrode lead 46 (the third substrate layer 3 is deformed by the presence of the printing film to become the reference electrode lead 46, and thus the printing films to become heater leads 71 located immediately thereunder are subjected to deformation due to the above deformation), thereby the resistance of the heater lead 71 having the overlapping part gets smaller.

As shown in FIG. 1, the measuring electrode lead 47 is provided on the first solid electrolyte layer 4 (between the first solid electrolyte layer 4 and the spacer layer 5), and the pump electrode lead 52 for the auxiliary pump electrode 51 is provided on the spacer layer 5 (between the spacer layer 5 and the second solid electrolyte layer 6). As shown in FIG. 3, the measuring electrode lead 47 is arranged at the position being apart from the perpendicular bisector P (at the position which is asymmetric). Nevertheless, the result shown in FIG. 5 indicates that the resistance values of the heater leads 71 are not affected if only the reference electrode lead 46 does not overlap any of the heater leads 71, even though those leads are arranged disproportionately.

As described above, according to the present embodiment, it can be obtained a state where the resistance value of each of two heater leads is equal to each other by arranging the reference electrode lead so as not to overlap any of two heater leads in the laminating direction in a cross-section perpendicular to the longitudinal direction of the sensor element. Therefore, the resistance value of the heater can be accurately obtained by measuring only the entire resistance values of the heater and two heater leads and the resistance value of one of the heater leads, thereby allowing temperature control of the sensor element more precisely.

<Variation>

The aforementioned present embodiment focuses on the relation of the reference electrode lead 46 and the heater leads 71. This is because it is the reference electrode lead 46 that is provided on the third substrate layer 3 laminated on the second substrate layer 2 on which the heater leads 71 are formed. If the sensor element 101 is designed to provide the other lead except the reference electrode lead 46 (e.g., the measuring electrode lead 47, the pump electrode lead 52, and the like) on the third substrate layer 3, the above other lead may be arranged so as not to overlap any of the heater leads 71 in the laminating direction, similarly to the aforementioned present embodiment.

While the invention has been shown and described in detail, the foregoing description is in all aspects illustrative and not restrictive. It is therefore understood that numerous modifications and variations can be devised without departing from the scope of the invention.

What is claimed is:

1. A gas sensor comprising:
   a sensor element composed of an oxygen ion conductive solid electrolyte, and
   a first power source and a second power source,
   said sensor element comprising:
      a plurality of solid electrolyte layers;
      a predetermined circuit pattern that is formed on each of the plurality of solid electrolyte layers wherein said gas sensor is formed by laminating a plurality of solid electrolyte layers together;
      an internal space to which the measurement gas is introduced;
      a reference gas space to which a reference gas is introduced;
      a plurality of pump electrodes provided to face each of said internal space and an external space;
      a measuring electrode provided to face said internal space;
      a reference electrode provided to face said reference gas space;
   wherein said sensor decomposes a predetermined gas component in a measurement gas, measures a current flowing within one of said oxygen ion conductive solid electrolyte layers during the decomposition of the predetermined gas component, and determines a concentration of the predetermined gas component based on the measured current,
   an oxygen partial pressure controlling pump cell composed of said plurality of pump electrodes and said oxygen ion conductive solid electrolyte existing among said plurality of pump electrodes, wherein said first power source applies a voltage to said oxygen partial pressure controlling pump cell to pump oxygen into and out of said internal space;
   a measuring pump cell composed of said measuring electrode, said reference electrode and said oxygen ion conductive solid electrolyte existing therebetween wherein said second power source applies a fixed voltage to said measuring pump cell, oxygen generated during the decomposition of the predetermined gas component is pumped out to said reference gas space and a current flowing by operation of the measuring pump cell is measured;
   a heater for electrically heating the proximity of said internal space, which is provided on a layer of said plurality of solid electrolyte layers;
   two heater leads having substantially the same shape which are energizing paths to said heater and provided on said layer;
   a first lead for electrically connecting said reference electrode to outside;
   a second lead for electrically connecting said measuring electrode to outside; and
   a third lead for electrically connecting said plurality of pump electrodes to outside;
   wherein said first lead is formed immediately above a first additional layer being a solid electrolyte layer laminated immediately above said layer, and arranged so as not to overlap any of said two heater leads in a laminating direction of said layer and said first additional layer, and one of said second lead and said third lead is formed immediately above a second additional layer that is a solid electrolyte layer laminated immediately above said first additional layer, a remaining one of said second lead and said third lead is formed immediately above a third additional layer that is a solid electrolyte layer laminated in direct contact with said second additional layer, and said second lead and said third lead are arranged so as not to overlap each other in said laminating direction when viewed in a lateral cross-sectional plane taken perpendicular to a longitudinal direction of the gas sensor, and
   wherein a resistance detecting lead is formed on said layer and is connected to one of said two heater leads by a connection part on said layer to measure the resistance of said one of said two heater leads.

2. The gas sensor according to claim 1, wherein at least one of said first lead, said second lead and said third lead is arranged between said two heater leads in a laminating direction in the lateral cross-sectional plane perpendicular to the longitudinal direction of the gas sensor.

3. The gas sensor according to claim 1, wherein said two heater leads are arranged on said layer so as to be axisymmetric in a longitudinal direction of said gas sensor.

4. The gas sensor according to claim 1, wherein said first lead is arranged between said two heater leads in a laminating direction when viewed in the lateral cross-sectional plane perpendicular to the longitudinal direction of the gas sensor.

5. The gas sensor according to claim 1, wherein said predetermined gas component is NOx.

6. A gas sensor composed of an oxygen ion conductive solid electrolyte, and said gas sensor comprising:
- a plurality of solid electrolyte layers;
- a predetermined circuit pattern that is formed on each of the plurality of solid electrolyte layers wherein said gas sensor is formed by laminating a plurality of solid electrolyte layers together;
- an internal space to which the measurement gas is introduced;
- a reference gas space to which a reference gas is introduced;
- a plurality of pump electrodes provided to face each of said internal space and an external space;
- a measuring electrode provided to face said internal space;
- a reference electrode provided to face said reference gas space;
- a first power source; and
- a second power source,
- wherein said sensor decomposes a predetermined gas component in a measurement gas, measures a current flowing within one of said oxygen ion conductive solid electrolyte layers during the decomposition of the predetermined gas component, and determines a concentration of the predetermined gas component based on the measured current,
- an oxygen partial pressure controlling pump cell composed of said plurality of pump electrodes and said oxygen ion conductive solid electrolyte existing among said plurality of pump electrodes, wherein said first power source applies a voltage to said oxygen partial pressure controlling pump cell to pump oxygen into and out of said internal space;
- a measuring pump cell composed of said measuring electrode, said reference electrode and said oxygen ion conductive solid electrolyte existing therebetween, wherein said second power source applies a fixed voltage to said measuring pump cell, oxygen generated during the decomposition of the predetermined gas component is pumped out to said reference gas space and a current flowing by operation of the measuring pump cell is measured;
- a heater for electrically heating the proximity of said internal space, which is provided on a layer of said plurality of solid electrolyte layers;
- two heater leads having substantially the same shape which are energizing paths to said heater and provided on said layer;
- a first lead for electrically connecting said reference electrode to outside;
- a second lead for electrically connecting said measuring electrode to outside; and
- a third lead for electrically connecting said plurality of pump electrodes to outside;
- wherein said first, second and third leads are each formed immediately above layers being solid electrolyte layers and different from one another,
- wherein one of said first, second and third leads is formed on a first additional layer laminated immediately above said layer, and arranged so as not to overlap any of said two heater leads when viewed in a lateral cross-sectional plane taken perpendicular to a longitudinal direction of the gas sensor,
- wherein a remaining one of said first, second and third leads is formed on a second additional layer that is a solid electrolyte layer laminated immediately above said first additional layer and a remaining one of said first, second and third leads is formed on a third additional layer that is a solid electrolyte layer laminated in direct contact with said second additional layer, and
- wherein a resistance detecting lead is formed on said layer and is connected to one of said two heater leads by a connection part on said layer to measure the resistance of said one of said two heater leads.

* * * * *